US00PP09338P

United States Patent [19]

Dehan

[11] Patent Number: Plant 9,338

[45] Date of Patent: Oct. 17, 1995

[54] IMPATIENS PLANT NAMED 'SWING'

[75] Inventor: Klara Dehan, Holon, Israel

[73] Assignee: Danziger "Dan" Flower Farm, Post Beit Dagan, Israel

[21] Appl. No.: 299,616

[22] Filed: Sep. 2, 1994

[51] Int. Cl.[6] ..... A01H 5/00

[52] U.S. Cl. ..... Plt./87.6

[58] Field of Search ..... Plt./87.6

*Primary Examiner*—James R. Feyrer

*Attorney, Agent, or Firm*—Foley & Lardner

[57] ABSTRACT

A new and distinct cultivar of Impatiens plant named Swing, characterized by its compact growth habit, excellent branching large, dark green leaves infused with purple, and its bicolor flowers, with the two pairs of petals being purple and a substantial part of the single larger petal and the flower center being a brighter red-purple.

1 Drawing Sheet

The present invention relates to a new and distinctive cultivar of Impatiens plant, botanically known as *Impatiens,* commercially known as New Guinea impatiens, and known by the cultivar name Swing.

The new cultivar was developed by the inventor Klara Dehan in Mishmar Hashiva, Israel in a controlled breeding program. The female or seed parent was a cultivar identified by the breeding number DC-4530, and the male or pollen parent was a cultivar identified by the breeding number DF-777. Both parents are proprietary cultivars used in the breeding program. The new cultivar was selected by the inventor from the progeny of the stated cross.

Asexual reproduction of the new cultivar by leaf cuttings performed by the inventor in Mishmar Hashiva, Isreal has established that the unique features of this new impatiens are stabilized and are reproduced true to type in successive propagations.

The following characteristics in combination distinguish the new Impatiens Swing from both its parent varieties and other cultivated impatiens of this type known and used in the floriculture industry:

1. Compact growth habit.
2. Excellent branching.
3. Large bicolor flowers, mainly purple in color, with bases of the petals and a substantial marking on the larger single petal being a brighter red-purple.
4. Large, dark green foliage, infused with purple.
5. Branching habit makes Swing particularly suited for hanging basket culture.

The accompanying color photographic drawing illustrates the overall appearance of the cultivar, with the colors being as true as it is reasonably possible to obtain in a colored reproduction of this type. The true flower color is not precisely illustrated in the color photograph, but is accurately indicated in the color values described below.

The following is a detailed description of the new impatiens cultivar based on plants produced under commercial practice in Mishmar Hashiva, Isreal. The plants described were grown in a net-covered greenhouse during the summer season with temperatures ranging from 35° C. maximum to 18° C. minimum. Color references are made to The Royal Horticultural Society Colour Chart except where general terms of ordinary dictionary significance are used.

Parentage: The female parent DC-4530 and the male parent DF-777 are seedlings from breeding program.

Propagation:

*Type cutting.*—Leaf cuttings.

*Time to initiate roots.*—7–8 days at 25° C. in summer; 8–9 days at 20° C. in winter.

*Rooting habit.*—Roots well.

Plant description:

*Form.*—Excellent self-branching produces a full, rounded symmetrical plant.

*Habit of growth.*—Compact growth habit.

*Foliage.*—Size: Large; mature leaves 10.0 cm long and 4.0 cm wide. Shape: Lanceolate to ovate. Margin: Serrated. Color: Young and mature foliage, top side 147A infused with purple; under side 187A. Venation: Purple.

Flowering description:

*Flowering habits.*—The initiation of flower buds takes about 4–5 weeks from potting leaf cutting. Flower completely opens approximately 10–11 weeks after potting.

*Natural flowering season.*—The new cultivar flowers under ambient conditions in Israel all year, but in the winter season with less light, there are fewer flowers.

*Flower buds.*—Buds before opening are approximately 2.0 cm in length and 1.5 cm in width. Length of spur is 4 cm and color of spur is purple; pedicel is 4.5 cm in length and light green.

*Flowers borne.*—Flowers carried on strong stems are fully open from initiation in about 2 weeks; flowering continues all season.

*Quantity of flowers.*—Very floriferous; 30–35 flowers open at the same time.

*Petals.*—Shape: Two (2) pairs of heart-shaped petals and a single larger petal; petals overlap. Color: Top side color on two (2) pairs of petals and a substantial portion of the single large petal is 78A, with center eye and a relatively large, irregular marking on the single larger petal being 74A; little or no fading as flowers mature; under side color is 71C; Number of petals: Five (5). Size of flowers: Large, about 6 cm in diameter.

*Reproductive organs.*—Stamens: One (1) in number. Anthers: Round, purple color. Pollen color: White. Pistils: Stigma: Round in shape, green in color. Ovaries: Four (4) in number, 1 mm in size; green in color.

Disease resistance: No significant disease problem noted to date.

I claim:

1. A new and distinct cultivar of Impatiens plant named Swing, as illustrated and described.

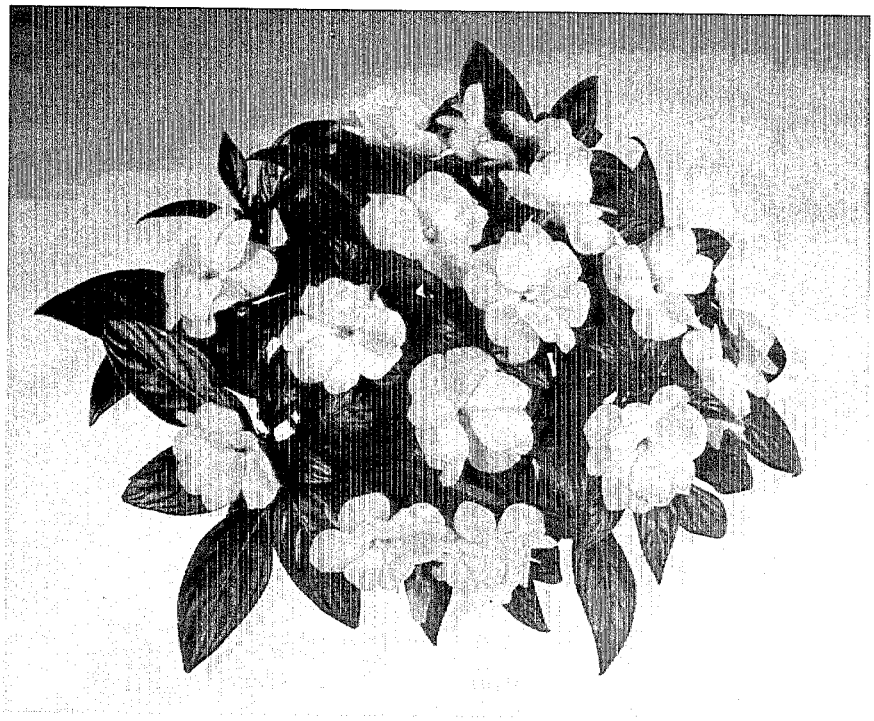

* * * * *